United States Patent [19]

Bonelli et al.

[11] Patent Number: 5,118,501
[45] Date of Patent: Jun. 2, 1992

[54] POLYPEPTIDIC COMPOSITION USEFUL FOR THE PREPARATION OF ANTIMALARIAL VACCINES AND OF DIAGNOSTIC KITS FOR THE DETECTION OF ANTIMEROZOITE ANTIBODIES

[75] Inventors: Fabio Bonelli; Antonello Pessi, both of Rome; Antonio S. Verdini, Monterotondo, all of Italy

[73] Assignee: Eniricerche S.p.A., Milan, Italy

[21] Appl. No.: 456,220

[22] Filed: Dec. 20, 1989

Related U.S. Application Data

[63] Continuation of Ser. No. 134,228, Dec. 17, 1987, abandoned.

[30] Foreign Application Priority Data

Dec. 23, 1986 [IT] Italy .................... 22820 A/86

[51] Int. Cl.$^5$ .................... A61K 39/00
[52] U.S. Cl. .................... 424/88; 514/13; 514/14; 530/324; 530/325; 530/326; 530/327; 530/328
[58] Field of Search .................... 424/88; 514/13, 14; 530/324–328

[56] References Cited

U.S. PATENT DOCUMENTS 4,806,348 2/1989 Hartl .................... 530/387

OTHER PUBLICATIONS

Ballou et al., Science, 228, 996–998, 1985.
Herzenberg et al., Nature, 285, 664–667, 1980.
Berzins, Proc. Natl. Acad. Sci., U.S.A., 83, 1065–1069, Feb. 1986.
Berzins et al., Chem. Abst., 104, 506 (1986), abst. No. 166578k.

Primary Examiner—Ronald W. Griffin
Attorney, Agent, or Firm—Shea & Gould

[57] ABSTRACT

Immunologically active polypeptide composition constituted by polypeptides having the formula:

$$H-(Glu-Glu-Asn-Val-Glu-His-Asp-Ala)_n-OH$$

wherein Glu = Glutamic Acid;
Asn = Asparagine;
Val = Valine;
His = Histidine;
Asp = Aspartic Acid;
Ala = Alanine and wherein n has a value equal to, or larger than, 2.

Said composition is useful for the preparation of antimalarial vaccines and of diagnostic kits for the detection of antimerozoite antibodies.

2 Claims, No Drawings

POLYPEPTIDIC COMPOSITION USEFUL FOR THE PREPARATION OF ANTIMALARIAL VACCINES AND OF DIAGNOSTIC KITS FOR THE DETECTION OF ANTIMEROZOITE ANTIBODIES

This application is a continuation of application Ser. No. 07/134,228, filed Dec. 17, 1987, now abandoned.

The present invention relates to an immunologically active polypeptidic composition useful for the preparation of antimalarial vaccines and of systems for the detection of antimerozoite antibodies in malariated individuals.

The invention relates furthermore to a method for the preparation of said composition.

The etiologic agent of malaria is a protozoan belonging to Plasmodium genus.

Among the hundreds of species of Plasmodium existing in nature, only four are pathogen for man: P. malariae, P. vivax, P. ovale, and P. falciparum.

This latter, in particular, represents the etiological agent of the most serious form of malaria, the so-said "tertian malignant malaria".

Notwithstanding the development of insecticides, and of drugs, such as chloroquine, malaria represents one of the most serious parasitic diseases for man.

Said disease is estimated in fact to strike, each year, a very large number of people, causing a mortality rate during the early infancy which can be as high as 50% of cases.

The need derives from the above, of developing an efficacious antimalarial vaccine, i.e., a vaccine which is capable of stimulating the production of antibodies which are able to attack and neutralize the parasite, and develop a permanent protective immunity.

The complexity of the vital cycle of the parasite, during which many modifications occur, both in morphology and in type of antigens produced, has made it difficult, up to the present time, to solve the problem of the vaccination.

These parasites, in fact, develop according to a multi-step cycle, partly inside the invertebrate host (anopheles mosquito), and partly inside the vertebrate host, exposing to the host a very large number of antigenic components different from one another, and step-specific.

The malarial infection in man begins with the bite of the anopheles mosquito, which releases, inside the blood stream, a certain number of sporozoites.

Within one hour, each sporozoite reaches a hepatic cell, wherein it will give rise to the formation of 20,000 or more merozoites.

Then, each merozoite, after leaving the hepatic cells, is capable of infecting an erythrocyte, wherein, through a series of transformations, it multiplies asexually, until the erythrocyte explodes, and releases from 10 to 20 merozoites.

Such a cycle of repeated breakage of the erythrocyte by the asexual parasites causes the clinic manifestations of malaria.

Some of said merozoites differentiate into male and female gametocytes, which represent the mosquito infecting form, and which will start the sexual cycle of the parasite.

In general, the development of an antimalarial vaccine is based on the identification and characterization of the only antigens of the parasite, which specifically stimulate immuno-protective responses.

During the past years, the researchers directed their attention to the identification of plasmodial antigens associated with the parasite forms exposed to the immunitary system and present both on the surface of the parasite, and on the membrane of the infected erythrocytes.

The development of an anti-erythrocytic-asexual-vaccine, capable of inhibiting this step of the vital cycle of the parasite, is particularly interesting, because it makes it possible the morbility and mortality due to the malarial disease, to be reduced.

Furthermore, said vaccine is useful for the treatment of persons highly exposed to the risk of contracting the parasitical infection in endemic regions, in that it is capable of inducing such a level of immunity, as to prevent the complications accompanying the malarial disease.

Recent studies have led to the identification and characterization, in many species of Plasmodium, of potentially protective antigens located on the surface of the asexual, erythocytic form of the parasite, and on the surface of the infected erythrocytes.

In particular, Perkins et al. (J. Exp. Med. 160, 788-789, 1984), and Coppel R.L. et al. (Nature 310, 789-792, 1984), identified and characterized an erythrocyte surface antigen (RESA) of P. falciparum, which is apparently released by the merozoites during the erythrocytic invasion.

Said antigen, which has a molecular weight of 155,000 daltons, is provided, in its C-terminal segment, with a region with repeated sub-units formed by 8, 4 and 3 aminoacids.

Studies carried out with antibodies against this antigen have shown that they inhibit, in vitro, the development of P. falciparum.

The synthesis of a peptide constituted by the sequence:

Glu-Glu-Asn-Val-Glu-His-Asp-Ala identical to the octapeptide belonging to a sub-unit of the C-terminal segment of RESA, is disclosed by Berzins et al., in Proc. Natl. Acad. Sci. USA 83 1065-1069, 1986. These Authors report furthermore that the peptide, when is conjugated to a carrier protein, induces, in test animals, the formation of antipeptide-antibodies capable of reacting with the whole protein.

Therefore, such a conjugate can be regarded as a good candidate for the development of an antimalarial vaccine.

However, the use of a peptide-macromolecular carrier obtained as above reported, poses particular problems in the development of a vaccine to be used on man.

In fact, it is known that synthetic vaccines containing an immunogen peptide bonded to a carrier, can be capable of expanding memory-B-cells, without stimulating antipeptide-T-cells.

This causes, in adult individuals with an acquired immunity towards the pathogen agent, a weak, or absent secondary immune response. From this, the need arises for an immunologically active peptide even in the absence of a conjugation with a carrier protein.

The present Applicant found now that it is possible to overcome the drawbacks of the prior art, by means of a polypeptidic composition, which is constituted by a mixture of polypeptides with a repeated aminoacidic sequence, which can be obtained in a pure form by a simple and economically favourable process.

A purpose of the present invention is therefore a polypeptidic composition useful for the preparation of antimalarial vaccines and of diagnostic kits for detecting antimerozoite antibodies in samples of blood from malariated individuals.

Also a purpose of the present invention is a process for the preparation of said polypeptidic composition.

Still another purpose of the present invention is also the use of said polypeptidic composition for preparing antimalarial vaccines and kits for detecting antimerozoite antibodies in samples of blood from individuals affected by the malarial disease.

Still further purposes of the invention will be clear from the following disclosure of the text and from the following Examples.

In particular, the polypeptidic composition according to the present invention is constituted by polypeptides which can be defined by means of the following general formula (I):

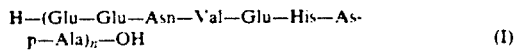

wherein: Glu = Glutamic Acid;
Asn = Asparagine;
Val = Valine;
His = Histidine;
Asp = Aspartic Acid;
Ala = Alanine and wherein n has a value equal to, or higher than, 2.

According to the present invention, said polypeptidic mixture can be prepared according to a process comprising:

a) the synthesis in the solid phase of an octapeptide whose side-chain carboxy functions of Asp and Glu are protected, having the following formula:

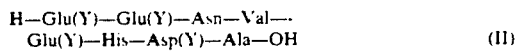

wherein Y is an acid-labile protecting group;

b) the release of octapeptide (II) from the resin, by means of the treatment with a weakly acidic solution;

c) the purification of octapeptide (II) by chromatography;

d) the polycondensation of the octapeptide (II) in an inert organic solvent, in the presence of an organic base, and of a polycondensation agent; a polypeptidic mixture is obtained:

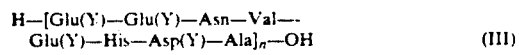

wherein Y is an acid-labile protecting group, and n has a value equal to, or larger than, 2;

e) the removal of the protecting groups from the side-chain carboxy functions of the polypeptidic mixture (III) by acidic cleavage;

f) the separation of the polypeptidic mixture

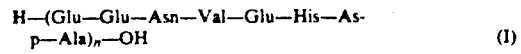

wherein n has a value equal to, or larger than, 2.

(a) STEP

In the (a) step of the process according to the present invention, the preparation of octapeptide (II) in protected form is carried out by condensation in solid phase, according to known general techniques.

Generally, the process is carried out by incorporating to an insoluble solid support the aminoacids, suitably protected at their α-aminogroup, and at their side-chain reactive functions, and activated at their end carboxy group, in the presence of condensation agents selected from those known in the art.

Solid supports are selected from polyamidic and/or polystyrenic resins, known to those skilled in the art.

In practice, a commercial polyamidic resin, which is already functionalized with norleucine as the internal reference aminoacid, and a hyper-acid-labile hook for the formation of the peptide-resin link, is used.

Protecting groups for the α-amino-group are selected from the base-labile groups, i.e., from those groups which can be removed by means of a basic hydrolysis.

Particularly preferred is fluorenyl-methoxy-carbonyl group (Fmoc).

Protecting groups for the pendant reactive functions are selected from those which are stable under the conditions of release of octapeptide from the resin.

A preferred example for such groups useful for the intended purpose is t-butyl group.

The aminoacids, suitably protected, are incorporated to the resin after the preliminary activation of their end carboxyl group, in the form of symmetrical anhydrides or phenyl esters, among which pentafluorophenyl is preferred. In case of Asn radical, 4-nitrophenyl ester is preferred.

The temperatures at which the esterification reaction is carried out can generally range from −10° C. to 40° C., and the corresponding times are the required times for completing, or substantially completing, the reaction.

Between a condensation reaction, and the next condensation reaction, the Fmoc protecting group is removed by means of a solution of piperidine-dimethylformamide, and washing of the peptide-resin.

(b) STEP

In the (b) step of the present invention, octapeptide (II) is removed from the resin, by means of a treatment with a weakly acidic solution.

In practice, a solution of $CH_2Cl_2$ at 1% in trifluoroacetic acid (TFA), at room temperature, is used.

The resin is then separated from the reaction mixture, by a direct filtration in dimethylformamide (DMF) in such a molar concentration, as to completely sequested trifluoroacetic acid (TFA).

Preferably, a molar excess of DMF relatively to TFA of 25-30 times the stoichiometric amount, is used.

The filtrates are then combined, the solvent is evaporated to dryness, and the residue is collected with a water-acetonitrile (1:1, volume/volume) solution, and is freeze-dried.

By operating as above shown, a release yield equal to, or larger than, 95% is obtained.

(c) STEP

In this step, octapeptide (II) is purified by High-Pressure-Liquid-Chromatography, using a resin of "reverse-phase" type, a mixture of $CH_3CH/H_2O/TFA$ mixture (45:54.9:0.9 volume/volume) as the eluent, and a flow rate of 9 ml/minute.

On HPLC, TLC, $_1$H-NMR analyses, the octapeptide results pure.

(d) STEP

In the (d) step of the process of the present invention, said octapeptide (II), in protected form, is condensed in the liquid phase in an inert (non-reactive) organic solvent, in the presence of excess amounts of a base of organic nature, and of a polycondensation agent.

Organic bases suitable for the intended purpose are the tertiary alkylamines, wherein the alkyl group is formed by a number of carbon atoms comprised within the range of from 1 to 4.

Particularly preferred is triethylamine.

Examples of polycondensation agents suitable for the intended purpose are selected from dicyclohexyl-carbodiimide (DCCI), DCCI+N-hydroxy-benzo-triazole, carbonyl-di-imidazole, and a certain number of active phosphorus compounds, such as, e.g., diphenyl-phosphorylazide, diethyl-phosphoro-cyano-hydrate, N-succinimido-diphenyl-phosphate, norborn-5-ene-2,3-dicarboxyimido-diphenyl-phosphate, and diphenyl-2-oxo-3-oxazolinylphosphate.

Among such agents, diphenyl-phosphoryl-azide (DPPA) is particularly suitable.

Inert organic solvents are selected from dimethyl-sulphoxide and dimethyl-formamide.

The reaction of polycondensation is carried out by using the maximum possible concentration of octapeptide (II) in organic solvent, in order to minimize the intramolecular cyclization reaction.

The temperatures at which the reaction of polycondensation is carried out can vary within the range of from $-10°$ to $50°$ C.

In practice, the reaction is carried out at a temperature of $40°$ C. for approximately 2 hours, and at room temperature ($20°-25°$ C.) for 72 hours, and, after the new addition of triethylamine and DPPA, still at room temperature for a further 72 hours.

(e) STEP

At the end of the reaction of polycondensation, in the (e) step of the process of the present invention, the protecting groups of the pendant carboxy groups are removed from the polypeptidic composition by means of a treatment with concentrated hydrochloric acid, and then with trifluoroactic acid, at room temperature.

(f) STEP

Finally, in the (f) step of the present invention, from the polypeptidic composition obtained as above, and purified by gel-chromatography, a mixture is separated, of polypeptides of the following formula:

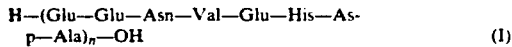
$$H-(Glu-Glu-Asn-Val-Glu-His-Asp-Ala)_n-OH \quad (I)$$

wherein n has a value equal to, or larger than, 2.

Said mixture can be used as such for preparing antimalarial vaccines, or in diagnostic kits for the determination of antimerozoite antibodies in clinical samples of malariated individuals.

As an alternative, said mixture can be fractionated into mixtures with a narrower molecular weight (MW) distribution.

The fractionation is carried out by gel-chromatography, using a Sephadex S-25 resin, a temperature of $20°-25°$ C., 0.1 M $CH_3COOH$ as the eluent, and a flow rate of 36 ml/hour.

By operating in that way, the fractions are separated and collected, which correspond to a molecular weight of approximately 4,800 daltons, with $n=5\pm1$, and fractions with a molecular weight of approximately 2,700 daltons, with $n=3\pm1$.

A mixture of polypeptides with a molecular weight of approximately 4,800 daltons, and with $n=5\pm1$ is particularly useful for the purposes of the present invention.

Both the global mixture, and the individual fractions show an immunogenic activity in test animals.

Particularly active is the fractions of polypeptides with $n=5\pm1$.

Therefore, all said polypeptides can be used for the preparation of antimalarial vaccines, and of diagnostic kits for the determination of antimerozoite antibodies in clinical samples from malariated persons.

The following experimental examples are illustrative and not limitative of the invention.

EXAMPLE 1

A) Synthesis of Protected Octapeptide

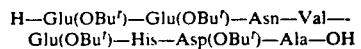
H—Glu(OBu$^t$)—Glu(OBu$^t$)—Asn—Val—
Glu(OBu$^t$)—His—Asp(OBu$^t$)—Ala—OH The synthesis is carried out by using an automatic Beckman synthetizer model 990 B, and a commercial polyamidic resin (CRB Pepsyn H) functionalized with norleucine, as the internal reference aminoacid, and 3-methoxy-4-hydroxymethyl-phenoxy-acetic acid as the reversible peptide-resin connection hook".

Two grams of said resin are swollen for 16 hours in 64 ml of N,N-dimethylformamide (DMF) at room temperature ($20°-25°$ C.), with the reactor being kept stirred.

The incorporation of the first aminoacid to the connection hook is carried out by means of the reaction of esterification, using the symmetrical anhydride of Ala aminoacid, protected on its α-amino group with fluorenyl-methyl-oxy-carbonyl protecting group (Fmoc-Ala)$_2$O.

2.17 g (3.6 mmol) of (Fmoc-Ala)$_2$O, 0.400 ml (3.6 mmol) of N-methylmorpholine (NMM), and 0.044 g (0.36 mmol) of 4-dimethylaminopyridine (DMAP) are dissolved, in this order, in 28 ml of DMF.

The esterification reaction is carried out at room temperature for approximately 30 minutes.

At the end of said reaction time, the Fmoc protecting group is removed by washing twice, i.e., respectively once for 3 minutes, and once for 7 minutes, the resin with piperidine-DMF (20:80, volume/volume).

Then, all of the other aminoacids are added, one at a time, according to the desired sequence, by means of the reaction of acylation between the activated carboxyl of the protected aminoacid, and the aminic group of the growing peptidic chain. Between an acylation reaction, and the next acylation reaction, intermediate washings are carried out, and the N-terminal Fmoc group is removed according to the following washing cycle: 10 washes with DMF, of 1 minute each; 1 wash with a (20:80, volume/volume) piperidine/DMF solution, for 3 minutes; 1 wash with a (20:80, volume/volume) piperidine/DMF solution, for 7 minutes; 10 washes with DMF, of 1 minute each.

The acylation reactions are carried out at room temperature, for 60 minutes.

The aminoacidic radicals Glu, Val, Asp and Ala are entered in the form of their symmetrical anhydride, prepared, immediately before the acylation reaction, by reacting 7.2 mmol of Fmoc-aminoacid with 3.6 mmol of dicyclohexyl-carbo-diimide (DCI), in 25 ml of $CH_2Cl_2$, at room temperature for 5 minutes. At the end of the reaction, dicyclohexyl-urea is filtered off, the solvent is evaporated off, and the symmetrical anhydride is recovered. is dissolved in DMF (30 ml). and is added to peptide-resin in the reactor.

The aminoacidic residue Asn is introduced in the form of 4-nitrophenylester in the presence of 0.488 g (3.6 mmol) of 1-hydroxybenzothiazol (HOBT).

The aminoacidic radical His is entered as Fmos-His(Trt)OH (Trt is triphenylmethyl protecting group) and is activated in situ. by directly charging to the reactor containing the peptide-resin, 2.26 g (3.6 mmol) of Fmoc-His(Trt)OH, 0.741 g (3.6 mmol) of DCI and 0.488 g (3.6 mmol) of HOBT, dissolved in 30 ml of DMF.

The completion of the acylation reaction is verified by means of the ninhydrin colorimetric test (E. Kaiser et al., Anal. Biochem., 34. 595, 1980). and by means of the tri-nitro-benzene-sulphonic acid test (W.S. Hancock et al., Anal. Biochem., 71, 261, 1976).

At the end of the assemblage of the sequence, the analysis of the peptide-resin for its aminoacidic content shows the following result:

| Asx | Glx | Ala | Val | His | Nle |
|---|---|---|---|---|---|
| 1.76(2) | 3.10(3) | 1.00 | 0.94(1) | 0.93(1) | 1.06 |

The theoretical values are in brackets.

| In the above table: | Asx: Asn + Asp; |
|---|---|
| | Glx: Glu + Gln. |

B) Removal of Octapeptide in Protected Form from the Resin

Octapeptide (II) is removed from the resin by means of the treatment with 250 ml of a solution of 1% of CH$_2$Cl$_2$ in trifluoroactic acid (TFA). at room temperature, for 1 hour.

The reaction mixture is then directly filtered into a flask containing a molar excess (25–30 times the stoichiometric amount) of DMF relatively to TFA.

The peptide-resin is again treated with 250 ml of a solution of CH$_2$Cl$_2$ at 1% in trifluoroactic acid (TFA), for 1 hour, and is filtered.

From the flask containing the combined filtrates the solvent is evaporated off. and the residue is collected in water-acetonitrile (50:50, volume/volume), and is freeze-dried.

The octapeptide removal percentage results, from the analysis of the residual resin, higher than 95%.

On $^1$H-NMR analysis, the recovered peptide results to contain, in fact, all of the t-butyl protecting groups, whilst, as desired, the imidazolic ring of histidine radical results free.

C) Purification of Protected Octapeptide (III)

The purification to homogeneity of the protected peptide is carried out by High-Pressure-Liquid-Chromatography (HPLC) on a Jobin-Yvon Miniprep preparative chromatograph, using Lichroprep RP-18 (25–40 µm) resin (Merck), CH$_3$CN/H$_2$O/TFA (45:54.9:0.1, volume/volume) as the eluent, and a flow rate of 9 ml/minute.

The fractions corresponding to the purified peptide are combined, freeze-dried. and the freeze-dried substance is characterized by HPLC, TLC and $^1$H-NMR analyses.

The analysis of the purified peptide for aminoacids gives the result:

| Asx | Glx | Ala | Val | His |
|---|---|---|---|---|
| 1.95(2) | 3.10(3) | 1 | 1.02(1) | 0.96(1) |

540 mg are obtained of purified peptide, with a chromatographic yield of 32%.

D) Polycondensation of Protected Octapeptide 100 mg (0.086 mmol) of purified octapeptide (II) are dissolved in 0.5 ml of dimethyl-sulphoxide (DMSO). To the solution, kept stirred, and maintained at the controlled temperature of 40° C., 31 µl (0.223 mmol) of triethyl-amine (TEA) and 24 µl (0.112 mmol) of diphenyl-phosphoryl-azide (DPPA) are added.

The so-obtained mixture is maintained, with stirring. at 40° C. for 2 hours, and then at room temperature (20°-25° C.) for a further 72 hours.

To said reaction mixture, triethyl-amine and diphenyl-phosphoryla-azide are then added. in the same proportions as above reported, and, after 72 hours at room temperature, 0.5 ml of concentrated HCl (32%, approx. 12 N) is added.

The reaction mixture is collected with concentrated HCl. water and dioxane, and is quantitatively transferred into a glass flask of 100 ml of capacity.

The solvent is evaporated off from the reaction mixture under vacuum, the residue is collected with 25 ml of TFA-water (90:10, volume/volume) solution, and the resulting solution is kept standing at room temperature for 30 minutes.

The solvent is then removed from the reaction mixture, the residue is collected with water, is filtered and is then freeze-dried.

E) Fractionation of Poly(Glu—Glu—Asn—Val—Glu—His—Asp—Ala) Composition

The so-obtained product (54.5 mg) is then fractionated by gel filtration on Sephadex G-50. and, subsequently, by chromatography on Sephadex G-25.

A column of 85×26 cm, packed with fine Sephadex G-50 resin (Pharmacia Uppsala) is used, eluted with 0.1 M CH$_3$COOH at the flow rate of 35 ml/hour.

Three fractions are thus obtained: the A fraction, 33.3 mg (35.4 mmol); the B fraction, 9.8 mg (10.4 mmol; and the C fraction, 0.5 mg (0.5 mmol), respectively corresponding to a mixture of polypeptides, wherein n is equal to, or larger than, 2; to the unreacted octapeptide; and to non-peptidic material.

The chromatographic yield is of 80%.

The A fraction is furthermore fractionated by using a column of 85×2.5 cm, packed with fine Sephadex G-25 resin, eluted with 0.1 M CH$_3$COOH, and with a flow rate of 36 ml/hour. By operating in such way, three fractions are obtained: the A' fraction, 2.6 mg (2.8 µmol); the A" fraction, 9.4 mg (10.0 µmol; and the A''' fraction, 15,0 mg (16.0 µmol), respectively corresponding to the polymer with an average molecular weight of approximately 4,800, which corresponds to n=5±1; to a polymer with an average molecular weight of approximately 2,700, which corresponds to n=3±1; and, finally, to the monomer (molecular weight=941).

The chromatographic yield resulted of 81%. The molecular weight of the individual fractions is determined by chromatography on agarose column in a medium with disaggregating and denaturing properties owing to the presence of 6 M guanidine chloride.

A column of 86×1.5 cm is used, which is packed with a Biogel A5M (100–200 mesh) resin, equilibrated with 6M guanidinium chloride, and eluted at the flow rate of 2.5 mh$^{-1}$. The column was calibrated by using a mixture of myoglobin (MW 18,000), Trypsin MW 8,000) and tryptophan (MW 200) as the standard.

The chromatography is performed at room temperature.

We claim:

1. An immunologically active polypeptide composition consisting essentially of a mixture of polypeptides of the formula:

$$H-(Glu-Glu-Asn-Val-Glu-His-Asp-Ala)_n-OH$$

wherein n is from 2-50.

2. An immunologically active composition as defined in claim 1 wherein at least 20% by weight of said polypeptides is a mixture of polypeptides wherein n is from 4 to 6.